US012697404B2

(12) United States Patent
Saidi et al.

(10) Patent No.: US 12,697,404 B2
(45) Date of Patent: Aug. 4, 2026

(54) PSMA-TARGETING CONJUGATE AND USES THEREOF

(71) Applicant: ORANO MED, Chatillon (FR)

(72) Inventors: Amal Saidi, Thonon-Les-Bains (FR); Amy Wong, Richardson, TX (US); Julien Torgue, Gaithersburg, MD (US); Tania Stallons, Wylie, TX (US)

(73) Assignee: ORANO MED, Chatillon (FR)

( * ) Notice: Subject to any disclaimer, the term of this patent is extended or adjusted under 35 U.S.C. 154(b) by 575 days.

(21) Appl. No.: 18/261,901

(22) PCT Filed: Jan. 17, 2022

(86) PCT No.: PCT/EP2022/050885

§ 371 (c)(1),
(2) Date: Jul. 18, 2023

(87) PCT Pub. No.: WO2022/157119

PCT Pub. Date: Jul. 28, 2022

(65) Prior Publication Data

US 2024/0100202 A1 Mar. 28, 2024

(30) Foreign Application Priority Data

Jan. 19, 2021 (EP) .................................... 21305061

(51) Int. Cl.
*A61K 51/04* (2006.01)
*A61P 35/00* (2006.01)

(52) U.S. Cl.
CPC .......... *A61K 51/0497* (2013.01); *A61P 35/00* (2018.01)

(58) Field of Classification Search
CPC ................ A61K 51/0497; A61K 51/00; A61K 51/0402; A61P 35/00; C07B 59/004; C07B 59/002; C07D 257/02; C07F 7/24
See application file for complete search history.

(56) References Cited

U.S. PATENT DOCUMENTS 11,541,133 B2 * 1/2023 Tworowska ........... A61K 47/22

FOREIGN PATENT DOCUMENTS

WO 2013082338 A1 6/2013
WO 2020083853 A1 4/2020

OTHER PUBLICATIONS

Sinnes et al., EJNMMI Radiopharmacy and Chemistry, vol. 5, No. 28, pp. 1-11 (Year: 2020).*
International Search Report for PCT/EP2022/050885 dated Mar. 3, 2022.
Written Opinion for PCT/EP2022/050885 dated Mar. 3, 2022.
Kozikowski, Alan P. et al., "Design of Remarkably Simple, Yet Potent Urea-Based Inhibitors of Glutamate Carboxypeptidase II (NAALADase)" J. Med. Chem. 2001, 44, pp. 298-301.
Eiber, Matthias et al., Prostate-Specific Membrane Antigen Ligands for Imaging and Therapy: J. Nucl. Med., 2017, vol. 58, No. 9 (Suppl. 2) pp. 67S-76S.
Noor, Asif et al. "Bivalent Inhibitors of Prostate-Specific Membrane Antigen Conjugated to Desferrioxamine B Squaramide Labeled with Zirconium-89 or Gallium-68 for Diagnostic Imaging of Prostate Cancer", Journal of Medicinal Chemistry, vol. 63, No. 17, Sep. 10, 2020 (Sep. 10, 2020), pp. 9258-9270.
Frei, Angelo et al. "Two is better than one: difunctional high-affinity PSMA probes based on a [CpM(CO) 3] (M = Re/99m Tc) scaffold", Dalton Transactions, vol. 48, No. 39, Oct. 7, 2019 (Oct. 7, 2019), pp. 14600-14605.
Schafer, Martin et al: "A dimerized urea-based inhibitor of the prostate-specific membrane antigen for 68 Ga-PET imaging of prostate cancer", EJNMMI Research Jun. 6, 2012, vol. 2, No. 23, pp. 2-11.
Nicholas, Zia et al. "A Bivalent Inhibitor of Prostate Specific Membrane Antigen Radiolabeled with Copper-64 with High Tumor Uptake and Retention", Angewandte Chemie International Edition, vol. 58, No. 42, Oct. 14, 2019 (Oct. 14, 2019), pp. 14991-14994.
Stenberg, Vilde Y., et al. "In situ Generated 212Pb-PSMA Ligand in a 224 Ra-Solution for Dual Targeting of Prostate Cancer Sclerotic Stroma and PSMA-positive Cells", Current Radiopharmaceuticals, Aug. 3, 2020 vol. 13, No. 2, pp. 130-141.
Sinnes, Jean-Philippe et al. "68Ga, 44Sc and 177Lu-labeled AAZTA5-PSMA617: synthesis, radiolabeling, stability and cell binding compared to DOTA-PSMA-617 analogues", EJNMMI Radiopharmacy and Chemistry, Nov. 26, 2020, vol. 5, No. 28, pp. 1-11.

* cited by examiner

*Primary Examiner* — D. L. Jones
(74) *Attorney, Agent, or Firm* — Chrisman Gallo Tochtrop LLC

(57) ABSTRACT

A PSMA-targeting conjugate or a pharmaceutically acceptable salt which may be used either for preparing a radiopharmaceutical or, once labeled with a radionuclide, as a radiopharmaceutical. The conjugate is of formula (I): $A^1$-$L^1$-Ch-$L^2$-$A^2$ (I)

wherein: Ch is a chelator, $L^1$ and $L^2$, identical or different, are a linker whereas $A^1$ and $A^2$, identical or different, are a urea-based PSMA ligand.

19 Claims, 7 Drawing Sheets

1 2 3 4 5

6

7

8

9a or

9b

Conjugate of formula (I)

PSMA-TARGETING CONJUGATE AND USES THEREOF

CROSS-REFERENCE TO RELATED APPLICATIONS

This is a National Stage application of PCT international application PCT/EP2022/050885, filed on Jan. 17, 2022, which claims the priority of European Patent Application No. 21305061.0, filed Jan. 19, 2021, both of which are incorporated herein by reference in their entirety.

TECHNICAL FIELD

The invention belongs to the field of radiopharmaceuticals.

More specifically, the invention relates to a PSMA-targeting conjugate or a pharmaceutically acceptable salt thereof and which may be used either for preparing a radiopharmaceutical or, once labeled with a radionuclide, as a radiopharmaceutical.

The invention also relates to a composition, a radiopharmaceutical as well as a kit-of-parts comprising the conjugate or the salt thereof.

The invention further relates to the use of the unlabeled conjugate or the salt thereof as well as of the kit-of-parts for preparing a radiopharmaceutical.

The invention still relates to the radiopharmaceutical for use in the in vivo imaging or the treatment of cancers in which the PSMA is overexpressed and, more particularly, prostate cancers.

BACKGROUND OF THE INVENTION

Prostate cancer is the most common cancer among men, except for skin cancer and the second leading cause of cancer death in men in the United States.

Several treatment options are presently proposed to prostate cancer patients depending on the type of cancer cells and the stage of development of the cancer, the age and the general health of the patients, such as active surveillance, surgery, external radiotherapy, cryotherapy, hormone therapy, high-intensity focused ultrasounds and chemotherapy.

Nevertheless, there is a strong need for improved therapy.

One promising way of improved therapy for prostate cancer leads is the use of targeting radiopharmaceuticals, that is to say of drugs which are labeled with a radionuclide and which are able to target the cancer cells so as to deliver a toxic level of radiation to the cancer cells whilst sparing normal healthy tissues.

Typically, radiopharmaceuticals designed to target prostate cancer cells are conjugates comprising a vector molecule with high affinity for prostate cancer cells and, possibly via a linker (or spacer), a chelator in which the radionuclide is retained by chelation.

PSMA, i.e. prostate-specific membrane antigen, also known as folate hydrolase I (FOLH1) and glutamate carboxypeptidase II (GCPII), is a trans-membrane glycoprotein which is primarily expressed in normal human prostate epithelium but which is overexpressed in prostate cancer, including metastatic cancer. Since PSMA is overexpressed in all prostate cancers and its expression is further increased in poorly differentiated, metastatic and hormone-refractory carcinomas, it is a very attractive target for cancer prostate imaging and therapy.

In the early 2000s, it has been shown that urea-based compounds, such as compounds comprising a glutamate-urea-glutamate or glutamate-urea-lysine motif, exhibit a particular high affinity for PSMA (cf. A. P. Kozikowski et al., *J. Med. Chem.* 2001, 44, 298-301; A. P. Kozikowski et al., *J. Med. Chem.* 2004, 47, 1729-1738).

Therefore, a variety of conjugates composed of three components, namely one urea-based PSMA ligand conjugated via one linker to one chelator for radiolabeling, such as DOTA, DOTAGA or HBED, has been proposed for targeting prostate cancer cells.

Such conjugates are notably the conjugate DOTA-PSMA-617, also known as PSMA-617, which is marketed as vipivotide tetraxetan, the conjugate DOTAGA-PSMA-I&T, also known as PSMA-I&T, as well as the conjugate PSMA-HBED-CC, also known as PSMA-11 (cf. Eiber et al., *J. Nucl. Med.,* 2017, 58, 9 (Suppl. 2)).

DOTA-PSMA-617, either labeled gallium-68 for imaging purpose or with lutetium-177 or actinium-225 for therapeutic purpose, has been particularly studied and is currently considered as one of the most promising conjugates for imaging and treating prostate cancers.

Yet, in the context of their work, the inventors have observed that, unexpectedly, the in vivo distribution profile as well as the in vivo efficacy of a three-component conjugate may be significantly improved if a second urea-based PSMA ligand is conjugated to the chelator via a second linker.

The invention is based on these experimental observations.

SUMMARY OF THE INVENTION

The invention firstly relates to a conjugate of formula (I) or a pharmaceutically salt thereof:

$$A^1\text{-}L^1\text{-Ch-}L^2\text{-}A^2 \quad (I)$$

wherein:

Ch is a chelator of formula (II) or (III):

(II)

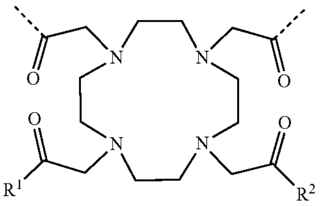

(III)

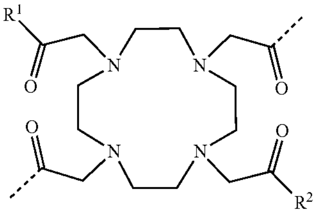

where:

the dotted lines represent the covalent bonds to $L^1$ and $L^2$;

$R^1$ and $R^2$ are, independently of one another, a —$NH_2$ or —OH group;

$L^1$ and $L^2$ are, independently of one another, a linker of formula (IV):

$$—NH—CH_2—Y—C(O)—NH—CH(R^5)—C(O)— \quad (IV)$$

where:

the dotted line at the left side of formula (IV) represents the covalent bond to Ch;

the dotted line at the right side of formula (IV) represents the covalent bond to $A^1$ for $L^1$ and to $A^2$ for $L^2$;

Y is an arylene group, a heteroarylene group or a ($C_5$-$C_8$)cycloalkylene group;

$R^5$ is an aryl group, a heteroaryl group, an aryl-($C_1$-$C_6$) alkyl group or a heteroaryl-($C_1$-$C_6$)alkyl group;

$A^1$ and $A^2$ are, independently of one another, a PSMA ligand of formula (V):

(V)

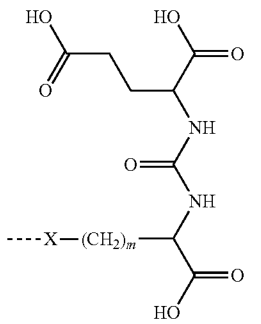

where:

the dotted line represents the covalent bond to $L^1$ for $A^1$ and to $L^2$ for $A^2$;

m is an integer from 2 to 6;

X is an oxygen atom, a sulphur atom, a divalent —NH— group or a divalent —N[$(CR^3R^4)_n$—Z]— group where $R^3$ and $R^4$ are independently H or a $C_1$-$C_3$ alkyl group, n is an integer from 1 to 3, and Z is a substituted or unsubstituted aryl group or heteroaryl group.

In what precedes and what follows:

the term "$C_1$-$C_3$ alkyl group" refers to a methyl, ethyl, n-propyl or isopropyl group;

the term "aryl group" refers to any group derived from a monocyclic or polycyclic aromatic hydrocarbon by removal of a hydrogen atom from a ring carbon atom (e.g. a phenyl, tolyl, xylyl, mesityl, naphthyl, biphenyl or anthracenyl group), whereas the term "heteroaryl group" refers to any aryl group such as just defined but whose ring or rings comprise(s) one or more heteroatoms, this or these heteroatoms typically being selected from among nitrogen, oxygen and sulphur atoms (e.g. a furyl, thiophenyl, pyrrolyl, pyridinyl, pyrazinyl, imidazolyl, pyrimidinyl, quinolinyl, isoquinolinyl, benzofuryl, isobenzofuryl, indolyl, isoindolyl or benzothiazolyl group); when substituted, the aryl or heteroaryl group may notably be substituted by a halogen atom such as a bromine, chlorine, iodine or fluorine atom;

the term "arylene group" refers to any divalent group derived from a monocyclic or polycyclic aromatic hydrocarbon by removal of a hydrogen atom from two ring carbon atoms (e.g. a phenylene group), whereas the term "heteroarylene group" refers to any arylene group such as just defined but whose ring or rings comprise(s) one or more heteroatoms, this or these heteroatoms typically being selected from among nitrogen, oxygen and sulphur atoms (e.g. a thienylene group);

the term "($C_5$-$C_8$)cycloalkylene group" refers to any divalent cycloalkyl group comprising 5, 6, 7 or 8 carbon atoms, i.e. a divalent cyclopentyl group (or cyclopentylene group), a divalent cyclohexyl group (or cyclohexylene group), a divalent cycloheptyl group (or cycloheptylene group) or a divalent cyclooctyl group (or cyclooctylene group);

the term "aryl-($C_1$-$C_6$)alkyl group" refers to any linear or branched alkyl group comprising 1, 2, 3, 4, 5 or 6 carbon atoms and whose at least one hydrogen atom is replaced with an aryl group, whereas the term "heteroaryl-($C_1$-$C_6$)alkyl group" refers to any linear or branched alkyl group comprising 1, 2, 3, 4, 5 or 6 carbon atoms and whose at least one hydrogen atom is replaced with a heteroaryl group.

In accordance with the invention, Ch meets preferably formula (III).

$R^1$ and $R^2$ are preferably identical to each other. More preferably $R^1$ and $R^2$ are a —$NH_2$ group.

Y is preferably a ($C_5$-$C_8$)cycloalkylene group, more preferably a cyclopentylene group (1,2-cyclopentylene or 1,3-cyclopentylene group) or a cyclohexylene group (1,2-cyclohexylene, 1,3-cyclohexylene or 1,4-cyclohexylene group) and, better still, a cyclohexylene group which is preferably a 1,4-cyclohexylene group.

$R^5$ is preferably an aryl-($C_1$-$C_6$)alkyl group, more preferably a naphthyl($C_1$-$C_3$)alkyl group such as a 1-naphthylmethyl, 1-naphthylethyl, 1-naphthyl-n-propyl, 2-naphthyl-methyl, 2-naphthylethyl or 2-naphthyl-n-propyl group, a 2-naphthylmethyl group being quite particularly preferred.

m is preferably 3 or 4, more preferably 4.

X is preferably a divalent —NH— group or a divalent —N[$(CH_2)_n$—Z]— group where n is as previously defined while Z is a phenyl group substituted by a halogen atom, a pyridinyl group substituted by a halogen atom or a quinolinyl group and, better still, a group of formula:

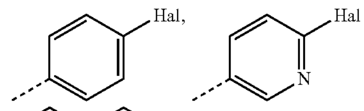

or

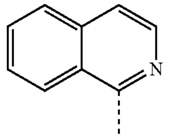

where:

the dotted line represents the covalent bond to $(CH_2)_n$,

Hal is a bromine, iodine or fluorine atom, preferably a bromine or iodine atom.

As previously mentioned, $L^1$ and $L^2$ may be identical to each other or different from each other. In a similar manner, $A^1$ and $A^2$ may be identical to each other or different from each other.

However, it is preferred that either $L^1$ and $L^2$ are identical to each other, or $A^1$ and $A^2$ are identical to each other or, better still, a combination of both.

According to another embodiment of the invention, $R^1$ and $R^2$ are a —OH group.

According to the invention, the conjugate is preferably the conjugate which meets formula (I) wherein:

Ch is of formula (III) where $R^1$ and $R^2$ are a —$NH_2$ group;

$L^1$ and $L^2$ are identical to each other;

Y is a 1,4-cyclohexylene group;

$R^5$ is a 2-naphthylmethyl group;

$A^1$ and $A^2$ are identical to each other;

m is 4; and

X is a —NH— group.

This conjugate, which is denoted hereinafter PSMA-OM-00214, meets particular formula (VI):

(VI)

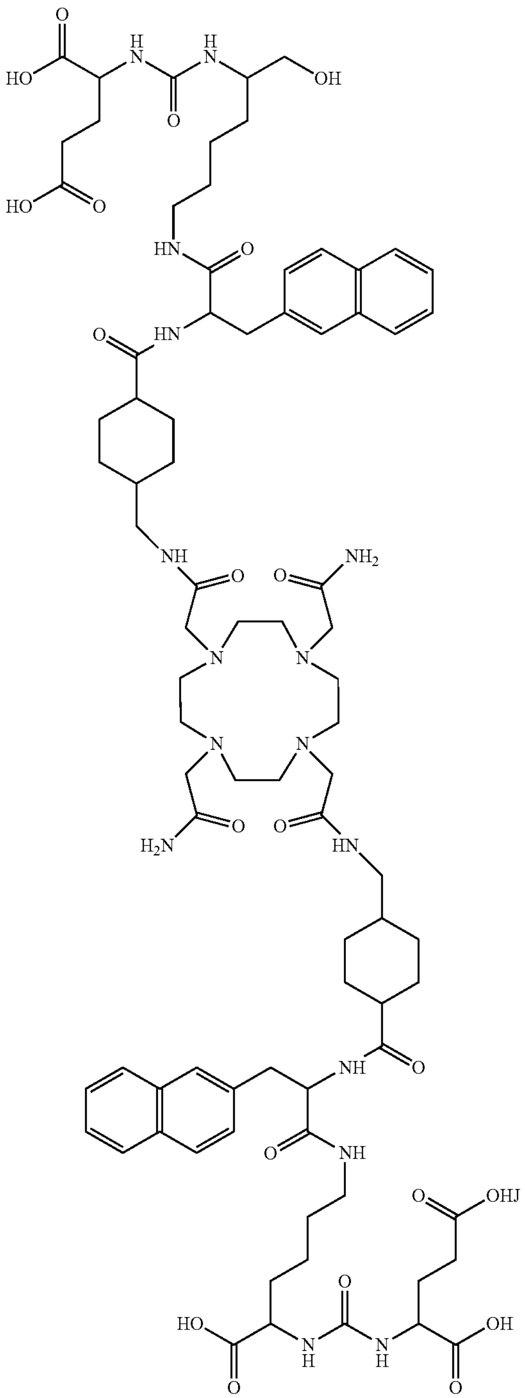

Suitable pharmaceutically-acceptable of the conjugate may notably be addition salts of free acids or free bases.

Acid addition salts may be prepared from an inorganic acid or from an organic acid. Appropriate inorganic acids include hydrochloric, hydrobromic, hydriodic, nitric, carbonic, sulfuric, and phosphoric acids, whereas appropriate organic acids may be selected from aliphatic, cycloaliphatic, aromatic, araliphatic, heterocyclic, carboxylic and sulfonic organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Base addition salts are, for example, metallic salts including alkali metal, alkaline earth metal and transition metal salts such as, for example, calcium, magnesium, potassium, sodium and zinc salts, or organic salts made from basic amines such as, for example, N,N-dibenzylethylenediamine, chloroprocaine, choline, diethanolamine, ethylenediamine, meglumine (N-methylglucamine) and procaine.

For use as a radiopharmaceutical, the conjugate or the salt thereof further comprises a radionuclide chelated by the chelator.

The invention also relates to a composition which comprises the conjugate or the salt thereof in unlabeled form (i.e. devoid of any radionuclide) in a pharmaceutically acceptable medium such as saline, metal-free water, ascorbic acid, ethanol, polysorbate 80 (i.e. polyoxyethylene (20) sorbitan monooleate, sold under the trademark Tween™ 80), a buffer such as an ammonium acetate buffer, or a mixture thereof, ascorbic acid and ethanol acting advantageously as antioxidants whereas polysorbate 80 reduces advantageously stickiness.

The invention further relates to a radiopharmaceutical ready for use, which comprises the conjugate or the salt thereof in radiolabeled form (i.e. comprising the radionuclide chelated by the chelator) in a pharmaceutically acceptable medium such as mentioned above.

The invention also relates to a kit-of-parts which may be used for preparing a radiopharmaceutical and which comprises at least:

- a first container containing the conjugate or the salt thereof in unlabeled form; and
- a second container containing the radionuclide, typically in the form of a salt (chloride, acetate, . . . ).

In the kits-of-parts, the conjugate or the salt thereof and the radionuclide may be in any appropriate form, such as in dry form (powder for example), a liquid form, i.e. in solution in a pharmaceutically acceptable medium such as mentioned above, or in a frozen form.

As known per se, the kit may further comprise:

- one or more reagents and/or one or more solvents or diluents such as saline, metal-free water, biological buffer and the like, and/or
- a booklet with instructions for preparing and/or using the radio-pharmaceutical, and/or
- accessories such as needles (for example, a venting needle), sterile filters, seals, quality control sampling items, etc. . . .

The invention further relates to the use of the unlabeled conjugate, the salt thereof or the kit-of-parts, for preparing a radiopharmaceutical, which use comprises a chelation of the radionuclide by the chelator of the conjugate or salt thereof.

In what precedes, the radionuclide is preferably a lead radionuclide, in particular $^{203}Pb$ if the radiopharmaceutical is intended to be used for in vivo imaging purposes or $^{212}Pb$ if the radiopharmaceutical is intended to be used for therapy purposes.

The invention still relates to the radiopharmaceutical for use in the in vivo imaging, for example by Single-Photon Emission Computed Tomography (SPECT), or the treatment of a cancer in which the PSMA is overexpressed.

Such a use comprises administering an appropriate dose of the radiopharmaceutical to the patient to be imaged or treated, typically intravenously, and, in case of an in vivo imaging, subjecting the patient to the imaging.

Preferably, the cancer is a prostate cancer, with or without metastases.

Other characteristics and advantages of the invention will become better apparent on reading the complement to the description that follows.

Obviously, this complement to the description is only given to illustrate the object of the invention and does not constitute in any case a limitation of said object.

BRIEF DESCRIPTION OF THE FIGURES

FIG. 4A illustrates the results in terms of survival, denoted S and expressed in %, of the mice as a function of time after injection of the cancer cells in the mice, denoted t and expressed in weeks, whereas FIG. 4B illustrates the results in terms of average tumor volume, denoted V and expressed in $mm^3$, as a function of time after injection of the cancer cells in the mice, denoted t and expressed in days.

DETAILED DESCRIPTION OF THE INVENTION

Figure 1:
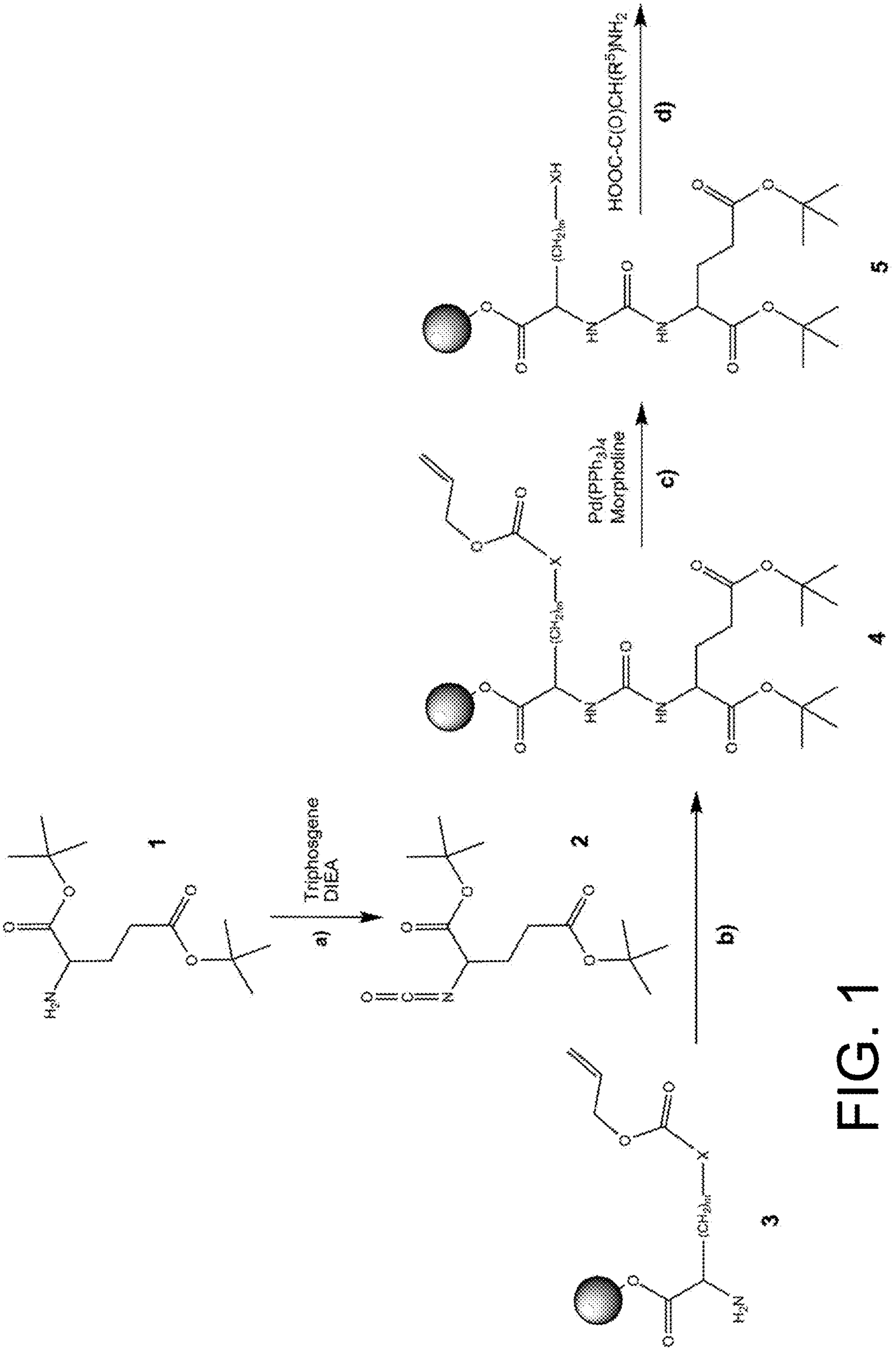
FIG. 1 illustrates a synthesis route of the conjugates of formula (I) in which $L^1$ and $L^2$ are identical to each other and $A^1$ and $A^2$ are identical to each other.
Figure 1:
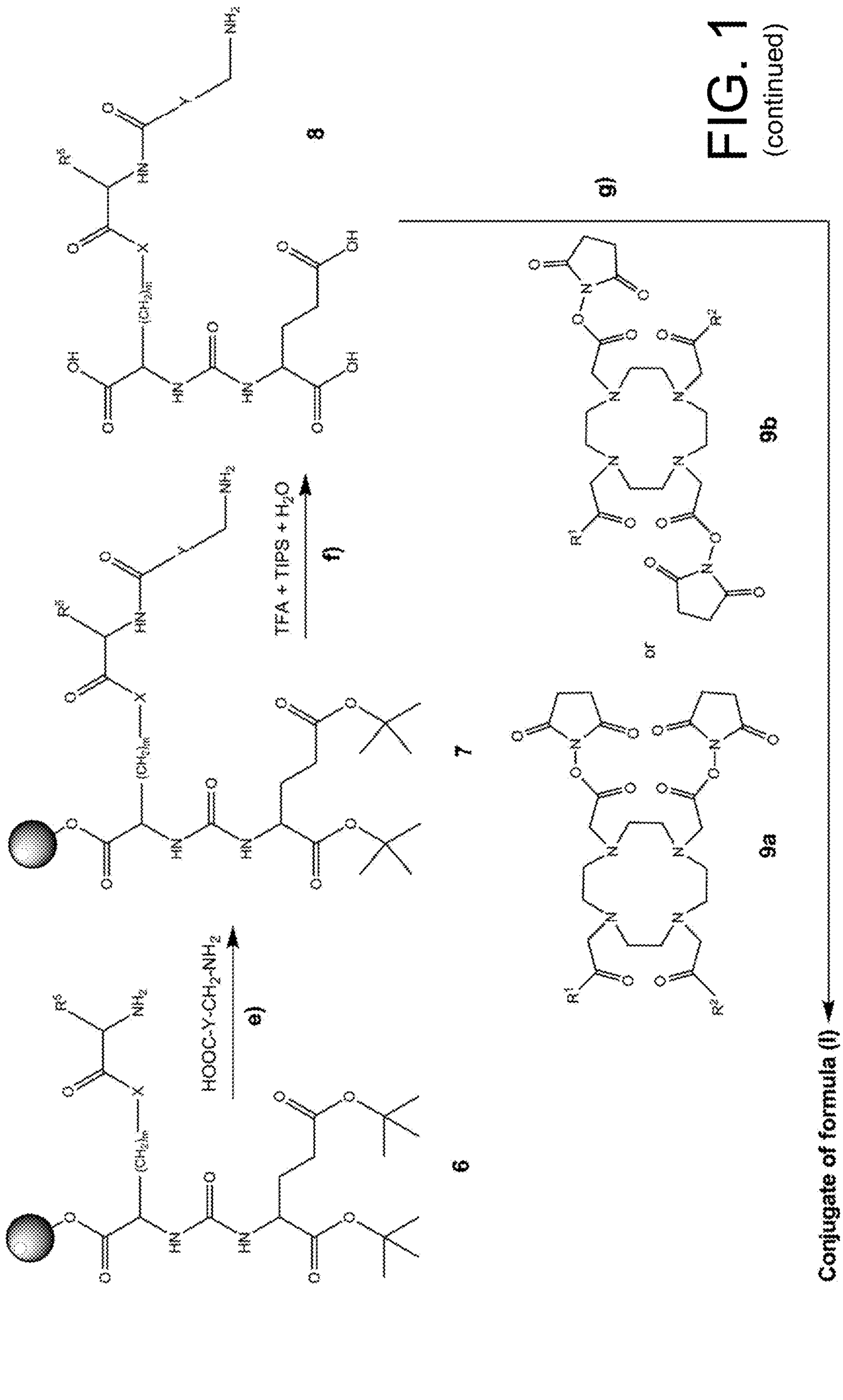

I—Synthesis of the Conjugates of Formula (I):

Conjugates of Formula (I) in which $L^1$ and $L^2$ are Identical to Each Other and $A^1$ and $A^2$ are Identical to Each Other:

Reference is made to FIG. 1 which illustrates the synthesis route by which any conjugate of formula (I) in which $L^1$ and $L^2$ are identical to each other and $A^1$ and $A^2$ are identical to each other may be obtained.

At a first step, denoted a) in FIG. 1, L-glutamic acid di-tert-butylester hydrochloride, denoted 1, is reacted with triphosgene and N-diisopropylethylamine (DIEA) in a polar aprotic solvent, such as dichloromethane (DCM), to give compound 2.

At a second step, denoted b), compound 2 is reacted with compound 3 resulting from the loading of a resin for solid phase peptide synthesis (represented as a grey disc), such as a 2-chlorotrityl chloride resin, with a compound of formula: $HOOC—CH(NH_2)—(CH_2)_m—X—C(O)—O—CH_2—CH{=}CH_2$ wherein m is as defined in formula (V) and X is O, S or —NH—, in a polar aprotic solvent, such as DCM, to yield compound 4.

At a third step, denoted c), the alloxycarbonyl group of compound 4 is cleaved by reaction with a nucleophilic compound able to accept an allyl group, such as morpholine or pyrrolidine, and a catalytic amount of a palladium complex, such as tetrakis(triphenyl-phosphine)palladium(0), in a polar aprotic solvent, such as DCM, to yield compound 5 wherein X is O, S or —NH—. If X is $—N[(CH_2)_n—Z]—$ in the conjugate to be synthesized, compound 5 wherein X is —NH— is further subjected to a reductive alkylation (not represented in FIG. 1) which is achieved by reacting compound 5 with an aldehyde of formula $CH(O)(CH_2)_{n'}—Z$ where n' is 1 or 2 and Z is as defined in formula (V), using a hydride, such as sodium borohydride, as a reducing agent, in methanol. Compound 5 wherein X is $—N[(CH_2)_n—Z]—$ is thus obtained.

At a fourth step, denoted d), compound 5 is coupled to a compound of formula: $HOOC—C(O)—CH(R^5)—NH_2$ wherein $R^5$ is as defined in formula (IV), to yield compound 6.

At a fifth step, denoted e), compound 6 is coupled to a compound of formula: $HOOC—Y—CH_2—NH_2$ wherein Y is as defined in formula (IV), to yield compound 7.

At a sixth step, denoted f), the peptidomimetic moiety of compound 7 is cleaved from the resin to yield compound 8.

At a seventh step, denoted g), compound 8 is conjugated to either compound 9a wherein $R^1$ and $R^2$ are as defined in formula (II) or compound 9b wherein $R^1$ and $R^2$ are as defined in formula (III) to yield the conjugate of formula (I) as a crude product.

The crude conjugate of formula (I) may be then purified by means of reverse-phase high performance liquid chromatography (HPLC).

Conjugates of Formula (I) in which $L^1$ and $L^2$ are Different from Each Other and/or $A^1$ and $A^2$ are Different from Each Other:

Any conjugate of formula (I) in which $L^1$ and $L^2$ are different from each other and/or $A^1$ and $A^2$ are different from each other may be obtained by synthesizing two compounds 8 differing from each other by the meanings of $L^1$ and $L^2$ and/or by the meanings of $A^1$ and $A^2$ by steps a) to f) as mentioned above, and by conjugating the so obtained compounds 8 simultaneously to either compound 9a or compound 9b.

The crude conjugate of formula (I) so obtained may be then purified by means of reverse-phase high performance liquid chromatography (HPLC).

II—Example of Implementing the General Synthesis Route to the Synthesis of PSMA-OM-00214:

The conjugate PSMA-OM-00214 (compound of formula (VI)) was synthesized by implementing the general synthesis route disclosed under item I above and shown in FIG. 1 as follows.

Preliminary step: preparation of compound 3 in which m is 4 and X is —NH—:

A 2-chlorotrityl chloride resin (available from Chem-Impex International, Inc., Cat: 03498) was loaded with $N^{\alpha}$-Fmoc-$N^{\epsilon}$-allyloxycarbonyl-L-lysine (more simply called Fmoc-L-Lys(Aloc)-OH and also available from Chem-Impex International, Inc., Cat: 03616).

To do that, the resin (10.4 meq., 6.9 g) was added to a 500 mL round bottom flask and was suspended in 100 mL of DCM. The mixture was spun for ≥20 minutes on a rotary evaporator at 140 rpm to allow for the resin swelling. To a 250 mL Erlenmeyer flask, the Fmoc-L-Lysine(Aloc)-OH (5.3 eq., 55.2 mmol, 25 g) was added to 100 mL of DCM. This was stirred for 40 minutes after which it was added to the resin in the form of a slurry along with DIEA (23.3 eq., 241.1 mmol, 42 mL). The Erlenmeyer flask was rinsed with 60 mL of DCM and this was added to the resin. The reaction was then allowed to spin on a rotary evaporator overnight. The following day, the resin was filtered on a course fritted funnel and washed with an excess of DCM. It was then dried under high vacuum for 6 hours until completely dry. A loading capacity of 0.84 meq/g was thus obtained. The Fmoc protecting group was removed by suspending the resin in 20% piperidine for 10 min before washing the resin with an excess of DCM.

Step a):

L-glutamic acid di-tert-butylester hydrochloride (Chem-Impex International, Inc., Cat: 03064-3 eq, 1.2 mmol, 354.96 mg) was reacted with triphosgene (0.33 eq., 0.4 mmol, 118.7 mg) and DIEA (2 eq., 0.6 mmol, 0.6 mL) in 80 mL of DCM at 0° C. for 4 hours, to yield compound 2.

Step b):

Compound 2 (0.2 mmol) was reacted with compound 3 (0.2 mmol) overnight in 80 mL of DCM to yield compound 4 in which m is 4, X is —NH—.

Step c):

The alloxycarbonyl protecting group of compound 4 was cleaved by reacting with tetrakis(triphenylphosphine)palladium(0) (0.02 eq., 0.004 mmol, 92.4 mg) and morpholine (0.03 eq., 0.006 mmol, 0.368 mL) in 15 mL of DCM at room temperature for 3 hours to yield compound 5 in which m is 4, X is —NH—.

Steps d) and e):

Fmoc-3-(2-naphthyl)-L-alanine (more simply called Fmoc-2-Nal—OH and available from Chem-Impex International, Inc., Cat: 02588) was coupled to compound 5 to yield compound 6 in which m is 4, X is —NH— and $R^5$ is a 1-naphtylmethyl group.

Then, trans-4-(Fmoc-aminomethyl)cyclohexane carboxylic acid (more simply called N-Fmoc-tranexamic acid and available from Sigma-Aldrich, Cat: 58446) was coupled to compound 6 to yield compound 7 in which m is 4, X is —NH—, $R^5$ is a 1-naphtylmethyl group and Y is a divalent cyclohexyl group.

Steps d) and e) were performed by means of the automated microwave peptide synthesizer Biotage™ Initiator+ Alstra™. Standard Fmoc chemistry was used with 2-(1H-benzotriazol-1-yl)-1,1,3,3-tetramethyluronium hexafluorophosphate (HBTU) as an activator.

Step f):

The peptidomimetic moiety of compound 7 was cleaved from the resin by suspending in a cocktail composed of 95% (v/v) of trifluoroacetic acid (TFA), 2.5% (v/v) of triisopropylsilane (TIPS) and 2.5% (v/v) of $H_2O$ to a final volume of 15 mL, to yield compound 8 in which m is 4, X is —NH—, $R^5$ is a 1-naphtylmethyl group and Y is a divalent cyclohexyl group.

The reaction was spun in a 50 mL round bottom flask for 3 hours after which the reaction medium was filtered over a course fritted funnel. The TFA was evaporated using $N^2$ gas and the crude product was precipitated using cold ethyl ether. The flask was then centrifuged at 4,500 rpm for 10 minutes and the ethyl ether supernatant was removed. The crude product was then freeze dried overnight to remove the excess of ethyl ether.

Step g):

Compound 8 (2.2 eq., 0.167 mmol, 110 mg) was reacted with compound 9b wherein $R^1$ and $R^2$ are —$NH_2$, i.e. DOTAM-1,10-diNHS-ester (1,4,7,10-tetraazacyclo-decane-4,7-di(carbamoylmethyl)-1,10-di-N-hydroxy-succinimidyl ester, available from Macrocyclics™-2.2 eq., 0.167 mmol, 110 mg) in 15 mL of 50 mM sodium bicarbonate buffer pH 7.5 for 24 hours, to yield crude conjugate PSMA-OM-00214.

Purification of Crude PSMA-OM-00214:

Crude PSMA-OM-00214 was purified by means of reverse-phase HPLC using a Phenomenex™ Luna™ 10 mm C18(2) preparative column (250×50 mm) with as a gradient: t=0-45 min: eluent A (0.1% TFA in water) with eluent B (0.1% TFA in acetonitrile (ACN)) rising linearly from 20% to 40% in eluent A.

PSMA-OM-00214 had a retention time of ≈29 min. The collected peak was submitted to a rotary evaporation to remove the organic solvent and freeze dried until dry.

It was thus obtained 7 mg of PSMA-OM-00214 with a purity >95% as determined with a Agilent™ 1100 Series LC-MS using a RESTREK™ Ultra IBD 3 μm analytical column (150×2.1 mm) with as a gradient: t=0-30 min: eluent A (0.1% TFA in ACN) with eluent B (100% water) rising linearly from 5% to 42.5% in eluent A.

The mass of PSMA-OM-00214 was confirmed with the Agilent™ 1100 Series LC-MS coupled with a Hewlett Packard™ 1100 Series MSD: expected 1677.89; observed 1677.65.

PSMA-OM-00214 was stored at −80° C. for later lead labeling.

III—Radiolabeling of PSMA-OM-00214:

For in vivo distribution and efficacy studies in mice, samples of PSMA-OM-00214 labeled with $^{212}$Pb, denoted hereinafter "$^{212}$Pb-PSMA-OM-00214", were prepared on the day of injection to the mice, chelated at the desired specific activity (i.e. the activity per ng of conjugate) and then diluted to achieve the required activity at time of injection.

For doing that, PSMA-OM-00214 as obtained under item II above was thawed and diluted in metal free water for injection. Then, an appropriate volume of the so obtained conjugate solution was added to cryogenic vials, possibly containing appropriate volumes of 0.4 M ammonium acetate, ascorbic acid, ethanol and Tween™ 80 solutions.

This was followed by an appropriate volume of a $^{212}$Pb-acetate solution (Orano Med).

The samples were incubated at 50° C. (unless otherwise noted) for 10 min and the chelation of $^{212}$Pb was verified by measuring the $^{212}$Pb remained free in the samples using instant thin layer chromatography (iTLC).

IV—In Vivo Studies with $^{212}$Pb-PSMA-OM-00214:

In what follows:

* the athymic nude mice used are Hsd:Athymic Nude-Foxn1$^{nu}$ mice from Envigo™;

the R2G2™ mice used are Rag2-IL2rg double knockout mice (B6;129-Rag2$^{tm1Fwa}$Il2rg$^{tm1Rsky}$/DwlHsd) from Envigo™;

the LNCaP human prostate cancer cells used are ATCC™ CRL1740™ cells from ATCC™; while the automatic gamma counter used is the Perkin Elmer™ Wizard$^{2}$™ counter.

IV.1—$^{212}$pb-PSMA-OM-00214 Biodistribution Study in Xenograft-Bearing Mice:

A study was carried out in order to assess the biodistribution of PSMA-OM-00214, labeled with $^{212}$Pb at a specific activity of 10 μCi per 10 ng of conjugate, in R2G2™ mice bearing a human prostate cancer cell tumor.

Study Design:

15 male R2G2™ mice, 7-8 weeks old and weighting 33.9±3.5 g at study initiation, were injected subcutaneously, into the right flank, with $10^6$ LNCaP cells in 100 μL of RPMI-1640 medium/Matrigel™ (v/v: 1/1). The tumors were let grow until they reached 200-300 mm$^3$ (as determined by the formula: volume=0.5×length×width$^2$).

Then animals were randomized based on tumor size and a group of 6 mice received intravenously (into a tail vein) one 10 μCi dose of $^{212}$Pb-PSMA-OM-00214 (10 μCi per 10 ng of conjugate, 100 μL injection volume).

The mice were sacrificed at 4 hour post-dose injection.

Blood, bladder, reproductive organs, small intestine, colon with caecum, spleen, pancreas, kidneys, stomach, liver, lung, heart, brain, femoral bone, abdominal fat, skeletal muscle, tail (as injection site) and LNCaP tumor were collected from each sacrificed mouse, weighted and transferred to individual tubes for automatic gamma counter.

The tubes were counted for two min. The background was automatically subtracted from the counts. A standard consisting of 5 μL of the solution injected to the mice was also counted for each group of mice and used for decay correction.

The percent injected dose per gram, denoted % ID/g, was calculated for each organ collected (mean±standard deviation).

Results

Figure 2:
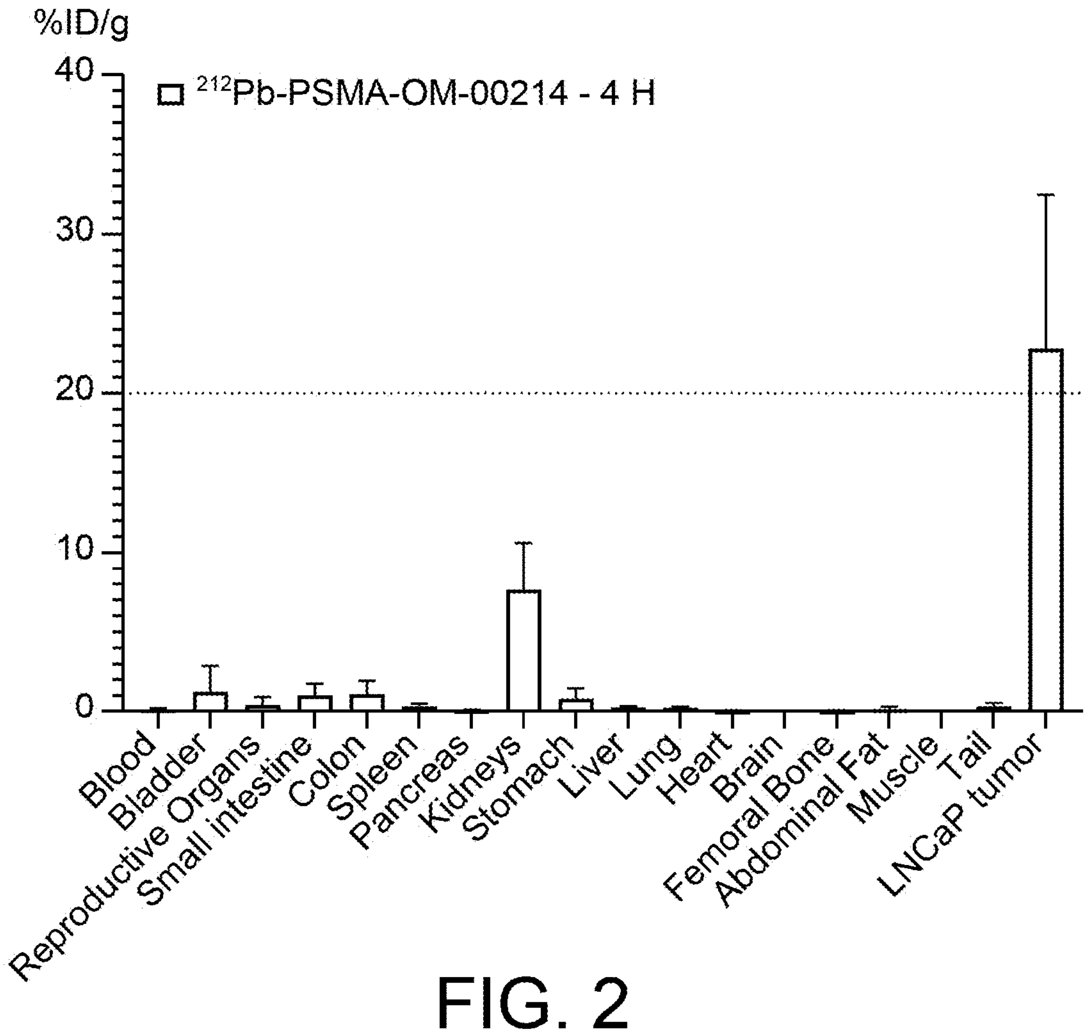
FIG. 2 illustrates the results of a biodistribution study made with the conjugate PSMA-OM-00214, labeled with $^{212}Pb$ at a specific activity of 10 μCi per 10 ng of conjugate, in R2G2™ mice bearing subcutaneous LNCaP tumors; the results are expressed in terms of percent injected dose per gram of organ, denoted % ID/g, as found in the organs of the mice at 4 hours after injection of the $^{212}Pb$-PSMA-OM-00214 doses in the mice.

The results as obtained are illustrated in FIG. 2.

As shown by this Figure, PSMA-OM-00214 has a favorable biodistribution profile with a very low uptake in all major non-tumor tissues and a satisfactory tumor/kidney ratio. The tumor uptake is more than 20% ID/g on average.

It is observable that the kidney uptake is as high as approximately 10% ID/g at 4 hours. This is accountable to both renal filtration and the well-described off-target binding to the kidneys by PSMA targeting agents.

IV.2—Comparative Biodistribution Study in Xenograft-Bearing Mice:

A study was carried out in order to compare the biodistribution of PSMA-OM-00214, labeled with $^{212}$Pb at a specific activity of 10 μCi per 10 ng of conjugate, in athymic nude mice bearing a human prostate cancer cell tumor with that of a conjugate, denoted hereinafter "DOTAM-PSMA-617", also labeled with $^{212}$Pb and differing from PSMA-OM-00214 in that it comprises only one PSMA ligand instead of two.

Thus, DOTAM-PSMA-617 is of formula:

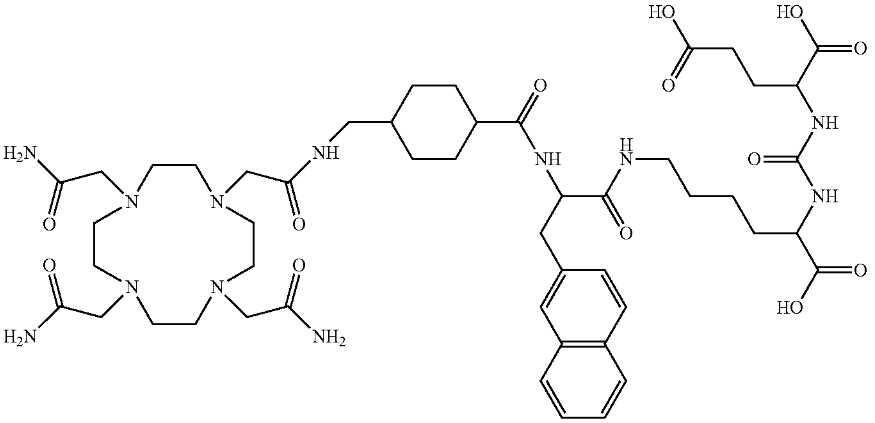 [SMILES: NC(=O)CN1CCN(CC(N)=O)CCN(CC(=O)NCC2CCC(C(=O)NC(Cc3ccc4ccccc4c3)C(=O)NCCCCC(NC(=O)NC(CCC(=O)O)C(=O)O)C(=O)O)CC2)CCN(CC(N)=O)CC1]

Preparation of $^{212}$Pb-DOTAM-PSMA-617:

Unlabeled conjugate DOTAM-PSMA-617 was prepared following the same protocol as described under item II above except that compound 8 was reacted with DOTAM-monoNHS-ester (1,4,7,10-tetraazacyclodecane-1,4,7-tri (carbamoylmethyl)-10-mono-N-hydroxysuccinimidyl ester), whereas labeling of DOTAM-PSMA-617 with $^{212}$Pb was made following the same protocol as described under item III above.

Study Design:

Three batches of male athymic nude mice, 7-8 weeks old and weighting 27.90±2.6 g for the first batch, 27.90±2.5 g for the second batch and 29.50±2.5 g for the third batch, at study initiation, were injected subcutaneously, into the right flank, with $10^6$ LNCaP cells in 100 μL of RPMI-1640 medium/Matrigel™ (v/v: 1/1). The tumors were let grow until they reached 200-300 mm$^3$.

The mice were divided into a plurality of groups each comprising 3 to 14 mice.

In any case, each mouse received intravenously either one 10 μCi dose of $^{212}$Pb-PSMA-OM-00214 (10 μCi per 10 ng of conjugate, 100 μL injection volume) or one 10 μCi dose of $^{212}$Pb-DOTAM-PSMA-617 (10 μCi per 10 ng of conjugate, 100 μL injection volume).

Some mice were sacrificed at 1 hour post-dose injection, others at 4 hours post-dose injection and still others at 24 hours post-dose injection.

Blood, reproductive organs, small intestine, colon with caecum, spleen, pancreas, kidneys, stomach, liver, lung, heart, brain, femoral bone, abdominal fat, skeletal muscle, tail, salivary glands and LNCaP tumor were collected from each sacrificed mouse, weighted and transferred to individual tubes for automatic gamma counter.

The tubes were counted for two min. The background was automatically subtracted from the counts. Standards consisting of 5 μL of the solutions injected to the mice were also counted and used for decay correction.

The percent injected dose per gram, denoted % ID/g, was calculated for each organ collected (mean±standard deviation).

Results

Figure 3A:
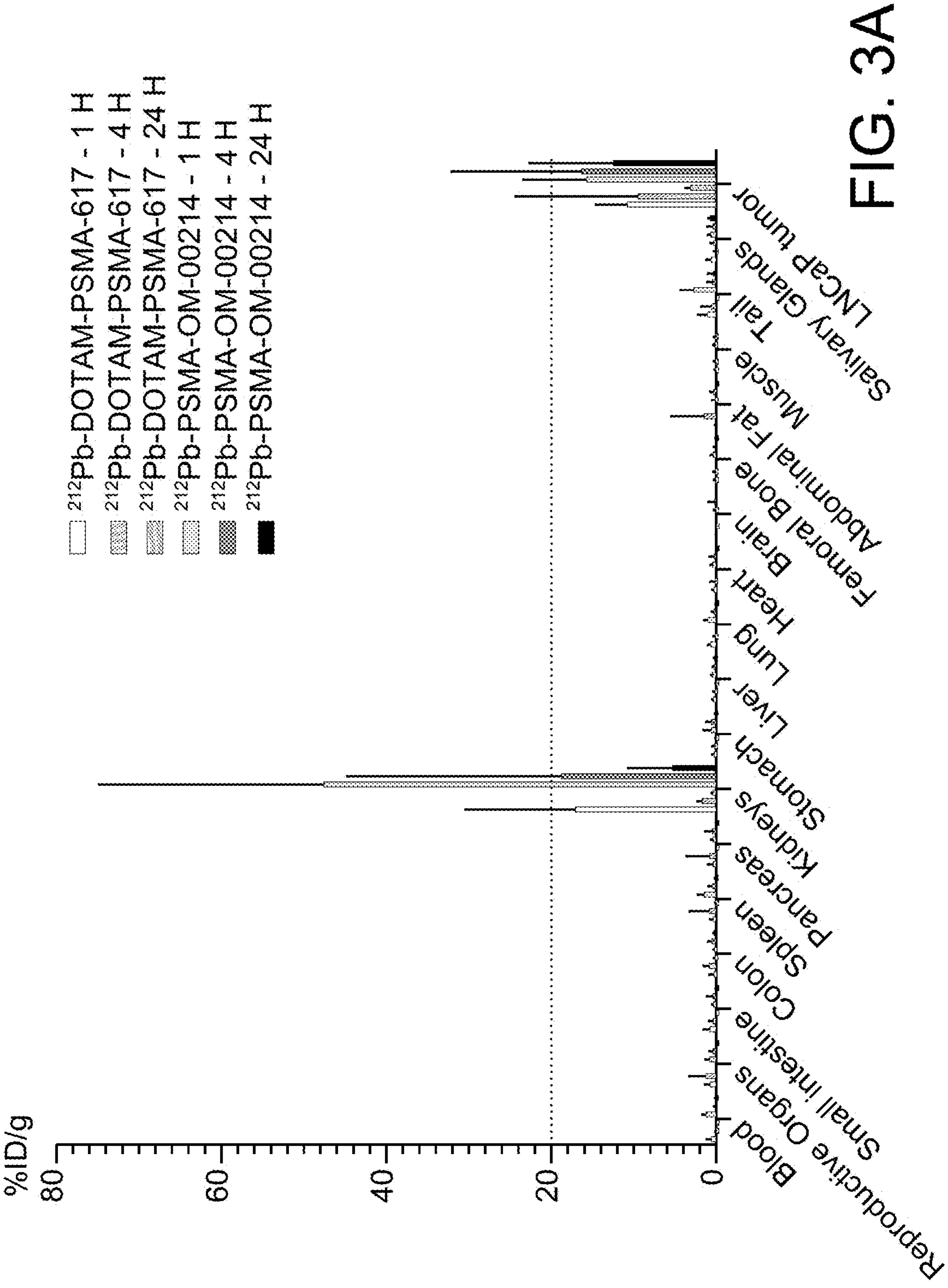
FIG. 3A illustrates the results of a comparative study aimed at comparing the biodistribution of the conjugate PSMA-OM-00214, labeled with $^{212}Pb$ at a specific activity of 10 μCi per 10 ng of conjugate, in athymic nude mice bearing subcutaneous LNCaP tumors with that of a conjugate, denoted DOTAM-PSMA-617, also labeled with $^{212}Pb$ at the same specific activity, and differing from PSMA-OM-00214 in that it comprises only one PSMA ligand linked to DOTAM; the results are expressed in terms of percent injected dose per gram of organ, denoted % ID/g, as found in the organs of the mice at 1 hour, 4 hours and 24 hours after injection of the $^{212}Pb$-conjugate doses in the mice.
Figure 3B:
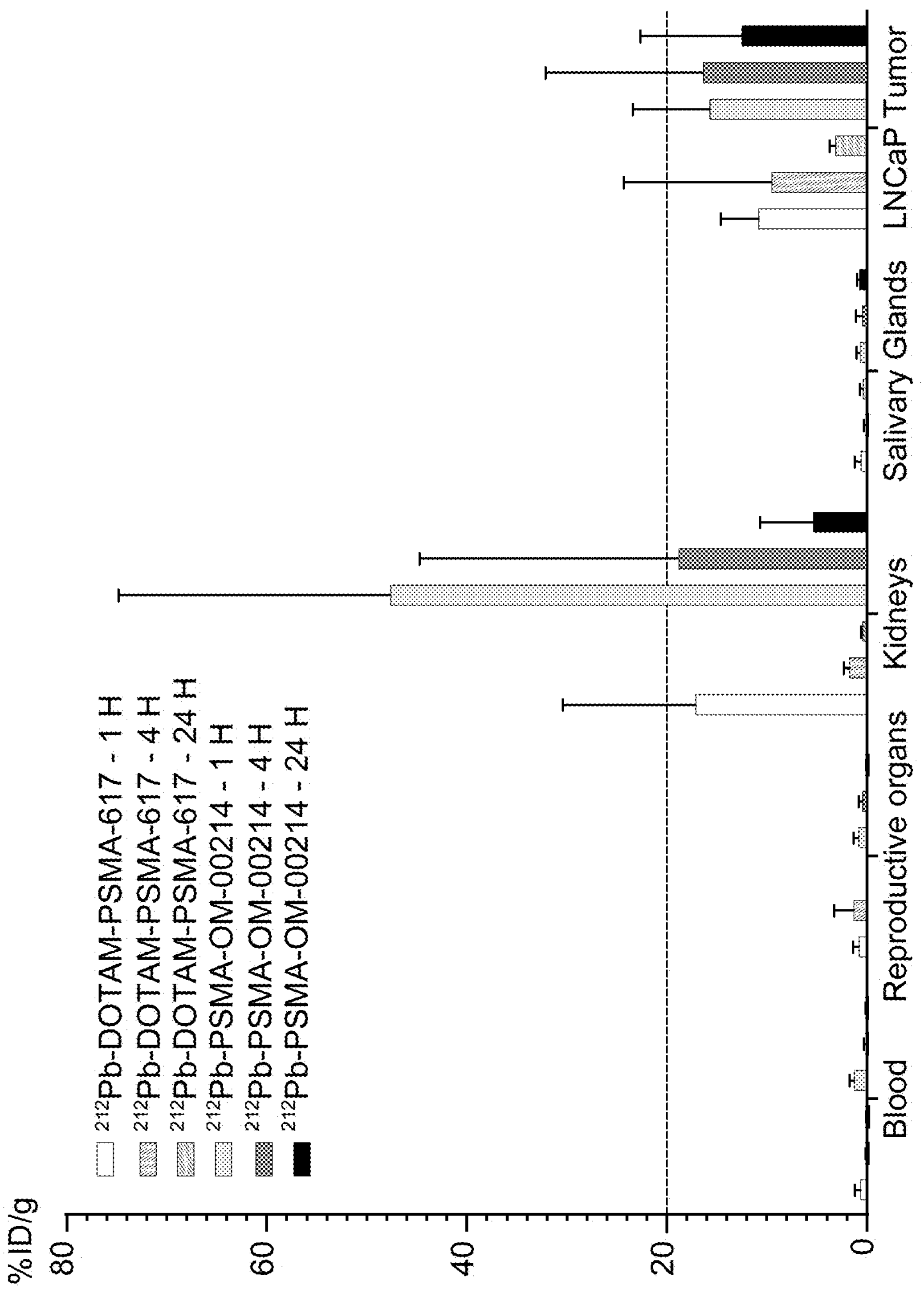
FIG. 3B illustrates the results shown in FIG. 3A but for a restricted number of organs.

The results are illustrated in FIGS. 3A (for all the collected organs) and 3B (for a restricted number of the collected organs).

As shown by these Figures, PSMA-OM-00214 has a superior in vivo distribution profile than DOTAM-PSMA-617 with a significantly higher tumor uptake and retention at 1 hour, 4 hours and 24 hours post-dose injection.

IV.3—Comparative Efficacy Study in Xenograft-Bearing Mice:

A study was carried out in order to assess the efficacy of one treatment cycle (cycle 1) or three treatment cycles (cycles 1, 2 and 3) using the conjugate PSMA-OM-00214, labeled with $^{212}$Pb at a specific activity of 10 μCi per 10 ng of conjugate, in R2G2™ mice bearing a human prostate cancer cell tumor and to compare this efficacy with that of three treatment cycles (cycles 1, 2 and 3) using the conjugate DOTAM-PSMA-617, also labeled with $^{212}$Pb at a specific activity of 10 μCi per 10 ng of conjugate.

Study Design:

Male R2G2™ mice, 7-8 weeks old and weighting 27.43±2.3 g, at study initiation, were injected subcutaneously, into the right flank, with $10^6$ LNCaP human prostate cancer cells in 100 μL of RPMI-1640 medium/Matrigel™ (v/v: 1/1). The tumors were let grow until they reached 200-300 $mm^3$.

Then, the mice were divided into 5 groups, respectively A, B, C, D and E, which were treated as follows:

Group A (15 mice): one 10 μCi dose of $^{212}$Pb-PSMA-OM-00214 (10 μCi per 10 ng of conjugate, 100 μL injection volume) at 24 days post-LNCaP cell injection (cycle 1);

Group B (15 mice): one 10 μCi dose of $^{212}$Pb-PSMA-OM-00214 (10 μCi per 10 ng of conjugate, 100 μL injection volume) at 24 days (cycle 1), 38 days (cycle 2) and 52 days (cycle 3) post-LNCaP cell injection respectively;

Group C (15 mice): one 10 μCi dose of $^{212}$Pb-DOTAM-PSMA-617 (10 μCi per 10 ng of conjugate, 100 μL injection volume) at 24 days (cycle 1), 38 days (cycle 2) and 52 days (cycle 3) post-LNCaP cell injection respectively;

Group D (10 mice): one 10 ng dose of unlabeled PSMA-OM-00214 (100 μL injection volume) at 24 days (cycle 1), 38 days (cycle 2) and 52 days (cycle 3) post-LNCaP cell injection respectively; and Group E (10 mice): 100 μL of buffer at 24 days, 38 days and 52 days post-LNCaP cell injection respectively.

During the study, the mice whose tumor volume reached 2 000 $mm^3$ were euthanized immediately. Furthermore, the mice were euthanized before the scheduled endpoint when they showed signs of unamenable distress or pain due to tumor burden, side effects of the injections, or a combination of two or more of the following termination criteria: acute weight loss (15% weight loss over two consecutive days or 20% weight loss from initial weight); poor tumor status (e.g. ulceration, teeth marks or open wounds); scruffiness/lack of grooming over 5 days; lethargy or reduced mobility over 3 days; weakness/balance issues over 5 days; hunchback appearance; diarrhea; paralysis; severe anemia and hypothermia).

Results

Figure 4A:
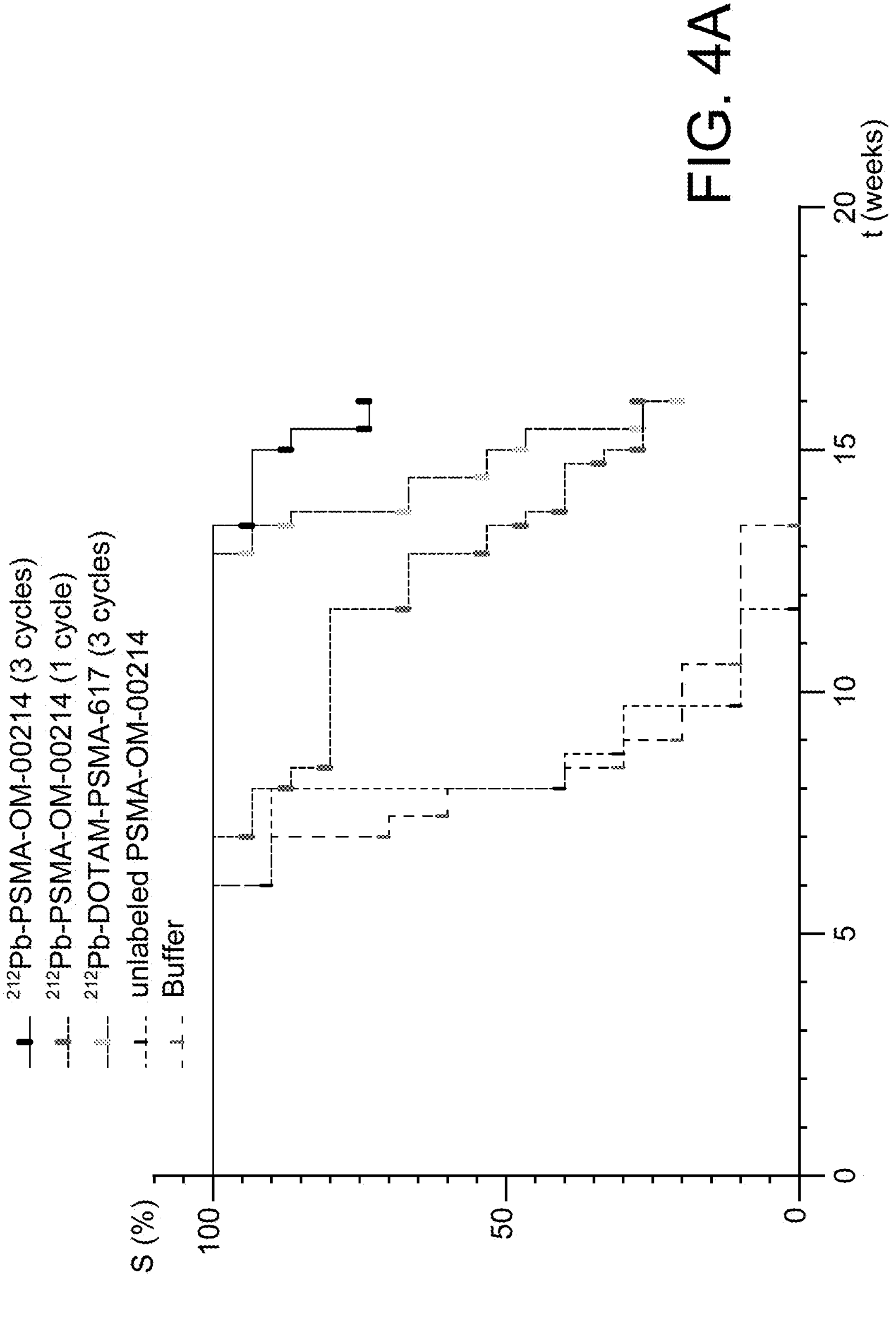
FIGS. 4A and 4B illustrate the results of a comparative study aimed at assessing the efficacy of one treatment cycle (cycle 1) or three treatment cycles (cycles 3) using the conjugate PSMA-OM-00214, labeled with $^{212}Pb$ at a specific activity of 10 μCi per 10 ng of conjugate, in R2G2™ mice bearing subcutaneous LNCaP tumors and at comparing this efficacy with that of three treatment cycles (cycles 3) using the conjugate DOTAM-PSMA-617, also labeled with $^{212}Pb$ at a specific activity of 10 μCi per 10 ng of conjugate.
Figure 4B:
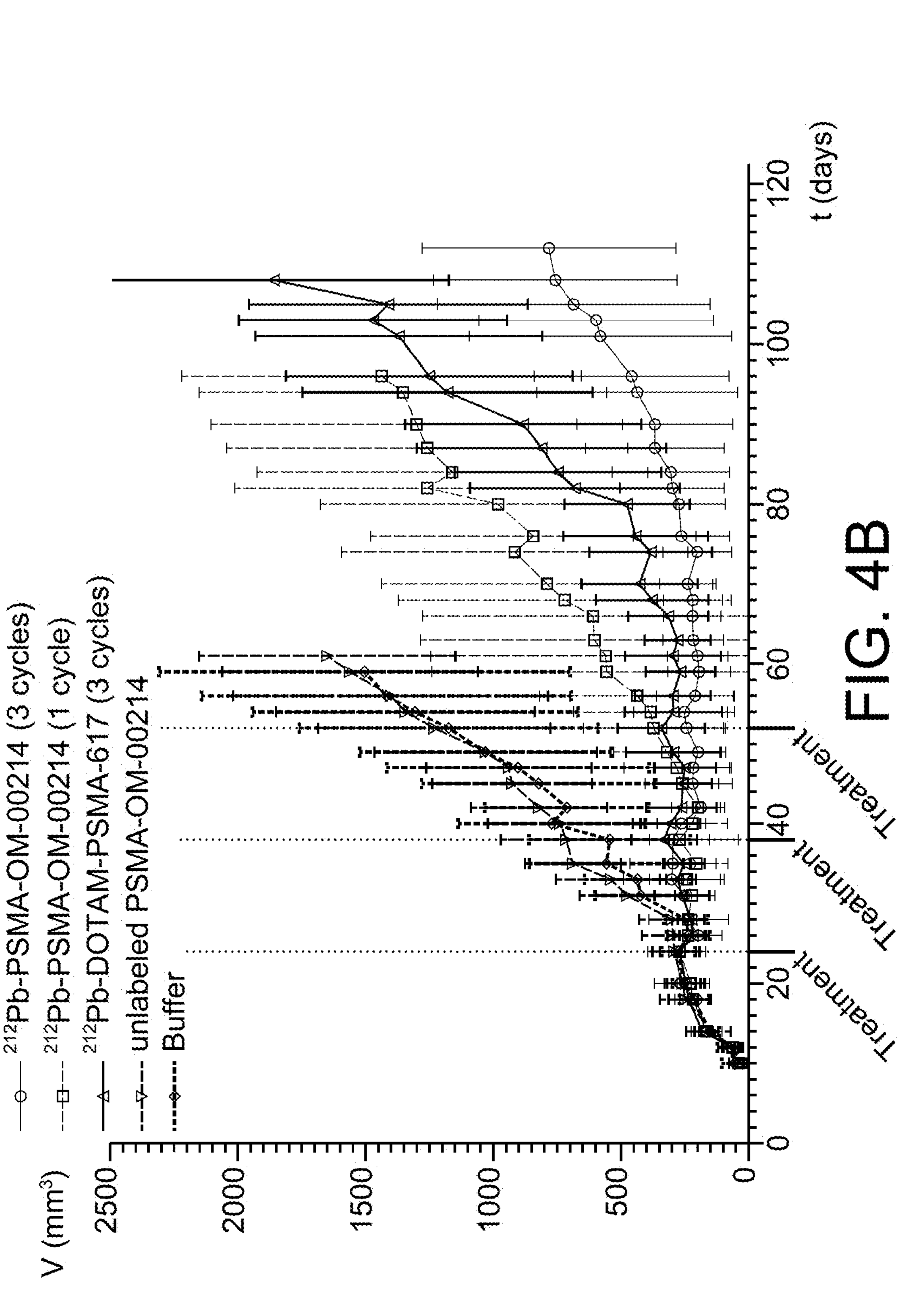

The results are illustrated in FIGS. 4A and 4B.

As shown by these Figures, administration of 3 cycles of $^{212}$Pb-PSMA-OM-00214 showed an important anti-tumor effect and a significantly prolonged survival compared to all other treatments. Survival was considerably extended, with the 3 cycles $^{212}$Pb-PSMA-OM-00214 treated group not reaching median survival over 15 weeks post-LNCaP cell injection whereas 1 cycle or $^{212}$Pb-DOTAM-PSMA-617 treatment resulted in a median survival of 13.4 and 15 weeks, respectively. Buffer and unlabeled controls both presented a median survival of 8 weeks.

What is claimed is:

1. A conjugate of formula (I) or pharmaceutically salt thereof:

$$A^1\text{-}L^1\text{-}Ch\text{-}L^2\text{-}A^2 \quad (I)$$

wherein:

Ch is a chelator of formula (II) or (III):

(II)

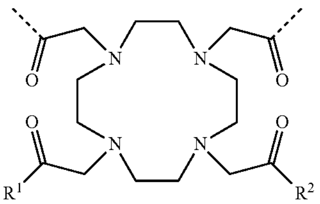

(III)

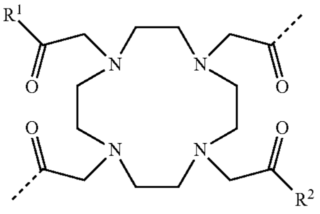

where:

the dotted lines represent the covalent bonds to $L^1$ and $L^2$;

$R^1$ and $R^2$ are, independently of one another, a —$NH_2$ or —OH group;

$L^1$ and $L^2$ are, independently of one another, a linker of formula (IV):

$$\text{—NH—CH}_2\text{—Y—C(O)—NH—CH(R}^5\text{)—C(O)—} \quad (IV)$$

where:

the dotted line at the left side of formula (IV) represents the covalent bond to Ch;

the dotted line at the right side of formula (IV) represents the covalent bond to $A^1$ for $L^1$ and to $A^2$ for $L^2$;

Y is an arylene group, a heteroarylene group or a $(C_5\text{-}C_8)$cycloalkylene group;

$R^5$ is an aryl group, a heteroaryl group, an aryl-$(C_1\text{-}C_6)$alkyl group or a heteroaryl-$(C_1\text{-}C_6)$alkyl group;

$A^1$ and $A^2$ are, independently of one another, a PSMA ligand of formula (V):

(V)

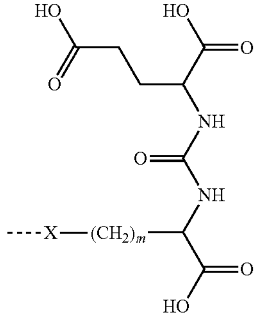

where:

the dotted line represents the covalent bond to $L^1$ for $A^1$ and to $L^2$ for $A^2$;

m is an integer from 2 to 6;

X is an oxygen atom, a sulphur atom, a divalent —NH— group or —N[$(CR^3R^4)_n$—Z]— group where $R^3$ and $R^4$ are independently H or a $C_1\text{-}C_3$ alkyl group, n is an integer from 1 to 3, and Z is a substituted or unsubstituted aryl group or heteroaryl group.

2. The conjugate or salt of claim 1, in which Ch is of formula (III).

3. The conjugate or salt of claim 1, in which:

$R^1$ and $R^2$ are identical to each other; and/or

Y is a cyclopentylene or cyclohexylene group; and/or $R^5$ is a naphthyl$(C_1\text{-}C_3)$alkyl group; and/or m is 3 or 4; and/or X is a divalent —NH— group or a divalent —N[$(CH_2)_n$—Z]— group where Z is a phenyl group substituted by a halogen atom, a pyridinyl group substituted by a halogen atom or a quinolinyl group.

4. The conjugate or salt of claim 1, in which:

$L^1$ and $L^2$ are identical to each other, and/or $A^1$ and $A^2$ are identical to each other.

5. The conjugate or salt of claim 1, in which:

Ch is of formula (III);

$R^1$ and $R^2$ are a —$NH^2$ group;

$L^1$ and $L^2$ are identical to each other;

Y is a 1,4-cyclohexylene group;

$R^5$ is a 2-naphthylmethyl group;

$A^1$ and $A^2$ are identical to each other;

m is 4; and

X is a —NH— group.

6. The conjugate or salt of claim 1, which further comprises a radionuclide chelated by the chelator.

7. The conjugate or salt of claim 6, in which the radionuclide is $^{203}Pb$ or $^{212}Pb$.

8. A composition, comprising a conjugate of formula (I) or pharmaceutically salt thereof:

$$A^1\text{-}L^1\text{-}Ch\text{-}L^2\text{-}A^2 \quad (I)$$

wherein:

Ch is a chelator of formula (II) or (III):

(II)

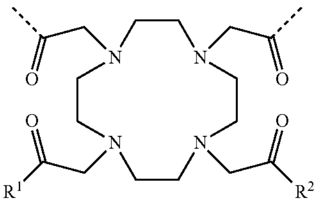

(III)

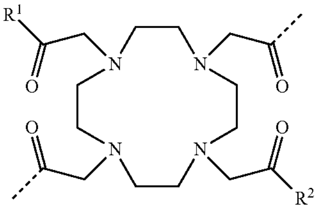

where:

the dotted lines represent the covalent bonds to $L^1$ and $L^2$;

$R^1$ and $R^2$ are, independently of one another, a —$NH_2$ or —OH group;

$L^1$ and $L^2$ are, independently of one another, a linker of formula (IV):

$$\text{—NH—CH}_2\text{—Y—C(O)—NH—CH(R}^5\text{)—C(O)—} \quad (IV)$$

where:

the dotted line at the left side of formula (IV) represents the covalent bond to Ch;

the dotted line at the right side of formula (IV) represents the covalent bond to $A^1$ for $L^1$ and to $A^2$ for $L^2$;

Y is an arylene group, a heteroarylene group or a $(C_5\text{-}C_8)$cycloalkylene group;

$R^5$ is an aryl group, a heteroaryl group, an aryl-$(C_1\text{-}C_6)$alkyl group or a heteroaryl-$(C_1\text{-}C_6)$alkyl group;

$A^1$ and $A^2$ are, independently of one another, a PSMA ligand of formula (V):

(V)

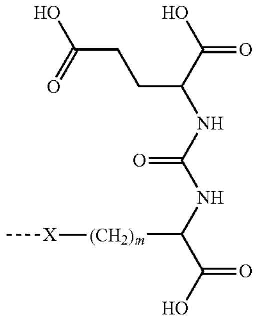

where:

the dotted line represents the covalent bond to $L^1$ for $A^1$ and to $L^2$ for $A^2$;

m is an integer from 2 to 6;

X is an oxygen atom, a sulphur atom, a divalent —NH— group or —N[$(CR^3R^4)_n$—Z]— group where $R^3$ and $R^4$ are independently H or a $C_1\text{-}C_3$ alkyl group, n is an integer from 1 to 3, and Z is a substituted or unsubstituted aryl group or heteroaryl group, in a pharmaceutically acceptable medium.

9. A radiopharmaceutical, comprising:

a conjugate of formula (I) or pharmaceutically salt thereof:

$$A^1\text{-}L^1\text{-}Ch\text{-}L^2\text{-}A^2 \quad (I)$$

wherein:

Ch is a chelator of formula (II) or (III);

(II)

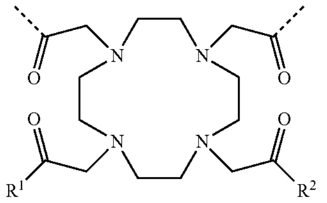

(III)

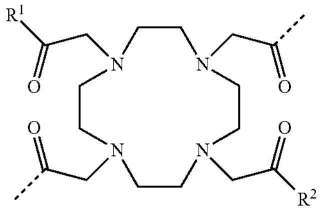

where:

the dotted lines represent the covalent bonds to $L^1$ and $L^2$;

$R^1$ and $R^2$ are, independently of one another, a $—NH_2$ or —OH group;

$L^1$ and $L^2$ are, independently of one another, a linker of formula (IV):

$$—NH—CH_2—Y—C(O)—NH—CH(R^5)—C(O)— \quad (IV)$$

where:

the dotted line at the left side of formula (IV) represents the covalent bond to Ch;

the dotted line at the right side of formula (IV) represents the covalent bond to $A^1$ for $L^1$ and to $A^2$ for $L^2$;

Y is an arylene group, a heteroarylene group or a $(C_5\text{-}C_8)$cycloalkylene group;

$R^5$ is an aryl group, a heteroaryl group, an aryl-$(C_1\text{-}C_6)$ alkyl group or a heteroaryl-$(C_1\text{-}C_6)$alkyl group;

$A^1$ and $A^2$ are, independently of one another, a PSMA ligand of formula (V):

(V)

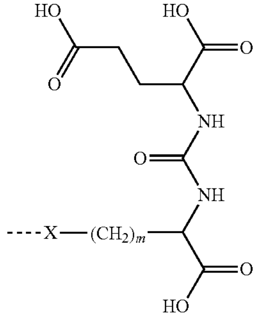

where:

the dotted line represents the covalent bond to $L^1$ for $A^1$ and to $L^2$ for $A^2$;

m is an integer from 2 to 6;

X is an oxygen atom, a sulphur atom, a divalent —NH— group or $—N[(CR^3R^4)_n—Z]—$ group where $R^3$ and $R^4$ are independently H or a $C_1\text{-}C_3$ alkyl group, n is an integer from 1 to 3, and Z is a substituted or unsubstituted aryl group or heteroaryl group; and a radionuclide chelated by the chelator;

in a pharmaceutically acceptable medium.

10. A kit-of-parts, which comprises at least:

a first container containing a conjugate of formula (I) or pharmaceutically salt thereof:

$$A^1\text{-}L^1\text{-}Ch\text{-}L^2\text{-}A^2 \quad (I)$$

wherein:

Ch is a chelator of formula (II) or (III):

(II)

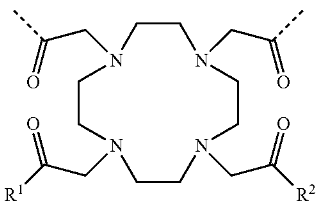

(III)

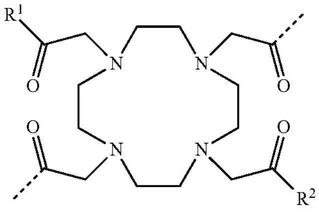

where:

the dotted lines represent the covalent bonds to $L^1$ and $L^2$;

$R^1$ and $R^2$ are, independently of one another, a $—NH_2$ or —OH group;

$L^1$ and $L^2$ are, independently of one another, a linker of formula (IV):

$$—NH—CH_2—Y—C(O)—NH—CH(R^5)—C(O)— \quad (IV)$$

where:

the dotted line at the left side of formula (IV) represents the covalent bond to Ch;

the dotted line at the right side of formula (IV) represents the covalent bond to $A^1$ for $L^1$ and to $A^2$ for $L^2$;

Y is an arylene group, a heteroarylene group or a $(C_5\text{-}C_8)$cycloalkylene group;

$R^5$ is an aryl group, a heteroaryl group, an aryl-$(C_1\text{-}C_6)$ alkyl group or a heteroaryl-$(C_1\text{-}C_6)$alkyl group;

$A^1$ and $A^2$ are, independently of one another, a PSMA ligand of formula (V):

(V)

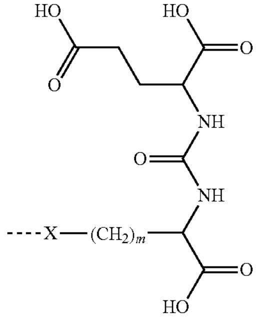

where:

the dotted line represents the covalent bond to $L^1$ for $A^1$ and to $L^2$ for $A^2$;

m is an integer from 2 to 6;

X is an oxygen atom, a sulphur atom, a divalent —NH— group or —N[$(CR^3R^4)_n$—Z]— group where $R^3$ and $R^4$ are independently H or a $C_1$-$C_3$ alkyl group, n is an integer from 1 to 3, and Z is a substituted or unsubstituted aryl group or heteroaryl group; and a second container containing a radionuclide.

11. The kit of claim 10, in which the radionuclide is $^{203}Pb$ or $^{212}Pb$.

12. A method for preparing a radiopharmaceutical from a conjugate of formula (I) or a pharmaceutically salt thereof:

$A^1$-$L^1$-Ch-$L^2$-$A^2$ (I)

wherein:

Ch is a chelator of formula (II) or (III):

(II)

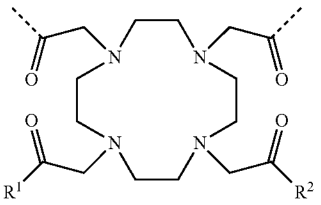

(III)

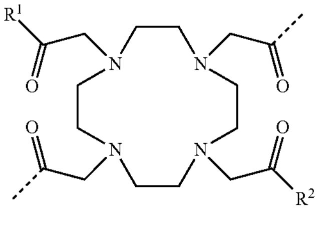

where:

the dotted lines represent the covalent bonds to $L^1$ and $L^2$;

$R^1$ and $R^2$ are, independently of one another, a —$NH_2$ or —OH group;

$L^1$ and $L^2$ are, independently of one another, a linker of formula (IV):

—NH—$CH_2$—Y—C(O)—NH—CH($R^5$)—C(O)— (IV)

where:

the dotted line at the left side of formula (IV) represents the covalent bond to Ch;

the dotted line at the right side of formula (IV) represents the covalent bond to $A^1$ for $L^1$ and to $A^2$ for $L^2$;

Y is an arylene group, a heteroarylene group or a ($C_5$-$C_8$)cycloalkylene group;

$R^5$ is an aryl group, a heteroaryl group, an aryl-($C_1$-$C_6$)alkyl group or a heteroaryl-($C_1$-$C_6$)alkyl group;

$A^1$ and $A^2$ are, independently of one another, a PSMA ligand of formula (V):

(V)

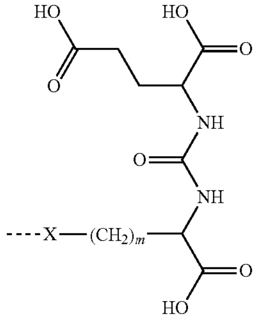

where:

the dotted line represents the covalent bond to $L^1$ for $A^1$ and to $L^2$ for $A^2$;

m is an integer from 2 to 6;

X is an oxygen atom, a sulphur atom, a divalent —NH— group or —N[$(CR^3R^4)_n$—Z]— group where $R^3$ and $R^4$ are independently H or a $C_1$-$C_3$ alkyl group, n is an integer from 1 to 3, and Z is a substituted or unsubstituted aryl group or heteroaryl group, comprising a chelation of a radionuclide by the chelator of the conjugate or salt thereof.

13. The method of claim 12, in which the radionuclide is $^{203}Pb$ or $^{212}Pb$.

14. A method for an in vivo imaging of a cancer in which the prostate-specific membrane antigen is over-expressed in a subject, comprising administering a radiopharmaceutical to the subject, the radiopharmaceutical comprising:

a conjugate of formula (I) or pharmaceutically salt thereof:

$A^1$-$L^1$-Ch-$L^2$-$A^2$ (I)

wherein:

Ch is a chelator of formula (II) or (III):

(II)

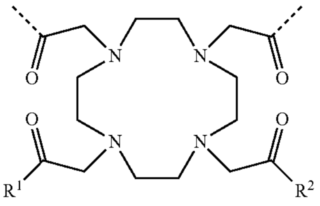

(III)

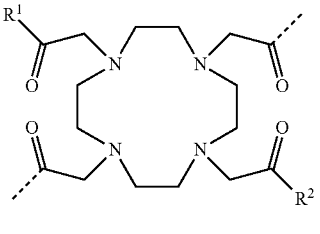

where:

the dotted lines represent the covalent bonds to $L^1$ and $L^2$;

$R^1$ and $R^2$ are, independently of one another, a —$NH_2$ or —OH group;

$L^1$ and $L^2$ are, independently of one another, a linker of formula (IV):

—NH—$CH_2$—Y—C(O)—NH—CH($R^5$)—C(O)— (IV)

where:

the dotted line at the left side of formula (IV) represents the covalent bond to Ch;

the dotted line at the right side of formula (IV) represents the covalent bond to $A^1$ for $L^1$ and to $A^2$ for $L^2$;

Y is an arylene group, a heteroarylene group or a ($C_5$-$C_8$)cycloalkylene group;

$R^5$ is an aryl group, a heteroaryl group, an aryl-($C_1$-$C_6$) alkyl group or a heteroaryl-($C_1$-$C_6$)alkyl group;

$A^1$ and $A^2$ are, independently of one another, a PSMA ligand of formula (V):

(V)

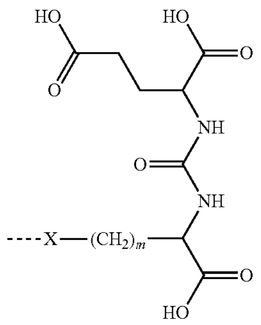

where:

the dotted line represents the covalent bond to $L^1$ for $A^1$ and to $L^2$ for $A^2$;

m is an integer from 2 to 6;

X is an oxygen atom, a sulphur atom, a divalent —NH— group or —N[($CR^3R^4$)$_n$—Z]— group where $R^3$ and $R^4$ are independently H or a $C_1$-$C_3$ alkyl group, n is an integer from 1 to 3, and Z is a substituted or unsubstituted aryl group or heteroaryl group; and a radionuclide chelated by the chelator;

in a pharmaceutically acceptable medium.

15. The pharmaceutical of claim 9, in which the radionuclide is $^{203}$Pb or $^{212}$Pb.

16. The method of claim 14, in which the radionuclide is $^{203}$Pb or $^{212}$Pb.

17. A method for treating a cancer in which the prostate-specific membrane antigen is over-expressed in a subject, comprising administering a therapeutically effective dosage of a radiopharmaceutical to the subject, the radiopharmaceutical comprising:

a conjugate of formula (I) or pharmaceutically salt thereof:

$A^1$-$L^1$-Ch-$L^2$-$A^2$ (I)

wherein:

Ch is a chelator of formula (II) or (III):

(II)

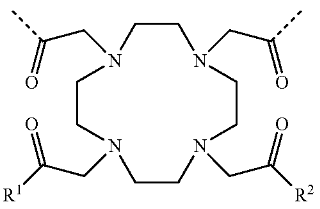

(III)

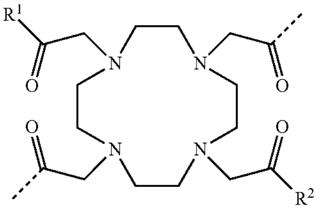

where:

the dotted lines represent the covalent bonds to $L^1$ and $L^2$;

$R^1$ and $R^2$ are, independently of one another, a —$NH_2$ or —OH group;

$L^1$ and $L^2$ are, independently of one another, a linker of formula (IV):

—NH—$CH_2$—Y—C(O)—NH—CH($R^5$)—C(O)— (IV)

where:

the dotted line at the left side of formula (IV) represents the covalent bond to Ch;

the dotted line at the right side of formula (IV) represents the covalent bond to $A^1$ for $L^1$ and to $A^2$ for $L^2$;

Y is an arylene group, a heteroarylene group or a ($C_5$-$C_8$)cycloalkylene group;

$R^5$ is an aryl group, a heteroaryl group, an aryl-($C_1$-$C_6$) alkyl group or a heteroaryl-($C_1$-$C_6$)alkyl group;

$A^1$ and $A^2$ are, independently of one another, a PSMA ligand of formula (V):

(V)

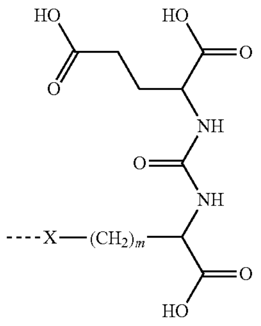

where:

the dotted line represents the covalent bond to $L^1$ for $A^1$ and to $L^2$ for $A^2$;

m is an integer from 2 to 6;

X is an oxygen atom, a sulphur atom, a divalent NH group or —$N[(CR^3R^4)_n$—Z]—group where $R^3$ and $R^4$ are independently H or a $C_1$-$C_3$ alkyl group, n is an integer from 1 to 3, and Z is a substituted or unsubstituted aryl group or heteroaryl group; and a radionuclide chelated by the chelator;

in a pharmaceutically acceptable medium.

18. The method of claim 17, in which the radionuclide is $^{203}Pb$ or $^{212}Pb$.

19. The method of claim 17, in which the cancer is a prostate cancer.

* * * * *